United States Patent
Kawamura et al.

(10) Patent No.: US 11,014,872 B1
(45) Date of Patent: May 25, 2021

(54) PRODUCTION METHOD FOR 1-AMINO CYCLOPROPANE CARBOXYLIC ACID NONHYDRATE

(71) Applicant: SUMITOMO CHEMICAL COMPANY, LIMITED, Tokyo (JP)

(72) Inventors: Mitsunobu Kawamura, Osaka (JP); Hiroaki Okamoto, Oita (JP); Kosuke Takebayashi, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 70 days.

(21) Appl. No.: 16/611,721

(22) PCT Filed: May 2, 2018

(86) PCT No.: PCT/JP2018/017482
§ 371 (c)(1),
(2) Date: Nov. 7, 2019

(87) PCT Pub. No.: WO2018/207694
PCT Pub. Date: Nov. 15, 2018

(30) Foreign Application Priority Data

May 8, 2017 (JP) .............................. JP2017-092615

(51) Int. Cl.
*C07C 227/42* (2006.01)
*C07C 227/18* (2006.01)

(52) U.S. Cl.
CPC .......... *C07C 227/42* (2013.01); *C07C 227/18* (2013.01); *C07B 2200/13* (2013.01)

(58) Field of Classification Search
CPC .. C07C 227/42; C07C 227/18; C07B 2200/13
See application file for complete search history.

(56) References Cited

U.S. PATENT DOCUMENTS

| | | | | |
|---|---|---|---|---|
| 4,367,344 A | * | 1/1983 | Gallenkamp | A01N 53/00 504/171 |
| 10,654,793 B2 | * | 5/2020 | Kawamura | C07C 227/38 |
| 2018/0282260 A1 | * | 10/2018 | Kawamura | A01N 53/00 |

FOREIGN PATENT DOCUMENTS

| | | |
|---|---|---|
| JP | 41-16862 B1 | 9/1966 |
| JP | 56-45443 A | 4/1981 |

OTHER PUBLICATIONS

Extended European Search Report for European Application No. 18798285.5, dated Feb. 1, 2021.
Valle et al., "Crystallographic characterization of conformation of 1-aminocyclopropane-l-carboxylic acid residue (Ac3c) in simple derivatives and peptides*," International Journal of Peptide and Protein Research, vol. 34, 1989, pp. 56-65, 10 pages total.
International Search Report, issued in PCT/JP2018/017482, PCT/ISA/210, dated Jul. 24, 2018.
Salaun et al., "A New and Convenient Preparation of 1-Aminocyclopropanecarboxylic Acid from Acrolein", J. Org. Chem., 1990, vol. 55, pp. 4276-4281.

* cited by examiner

*Primary Examiner* — Yevgeny Valenrod
*Assistant Examiner* — Blaine G Doletski
(74) *Attorney, Agent, or Firm* — Birch, Stewart, Kolasch & Birch, LLP

(57) ABSTRACT

1-Aminocyclopropanecarboxylic acid non-hydrate can be obtained by treating 1-aminocyclopropanecarboxylic acid hydrochloride with a tertiary amine in the presence of a $C_3$-$C_4$ alcohol and water, keeping the reaction mixture at 50° C. or below, collecting the precipitated crystal of 1-aminocyclopropanecarboxylic acid 0.5 hydrate by filtration, and contacting the obtained crystal with a $C_1$-$C_2$ alcohol.

3 Claims, 2 Drawing Sheets

PRODUCTION METHOD FOR 1-AMINO CYCLOPROPANE CARBOXYLIC ACID NONHYDRATE

TECHNICAL FIELD

The present invention relates to production of 1-aminocyclopropanecarboxylic acid non-hydrate.

BACKGROUND ART

1-Aminocyclopropanecarboxylic acid is known as a plant growth regulator.

A production method of 1-aminocyclopropanecarboxylic acid hydrochloride is known in Patent Document 1 and Non-Patent Document 1. A method of converting 1-aminocyclopropanecarboxylic acid hydrochloride into a free form of 1-aminocyclopropanecarboxylic acid is also described in Patent Document 1 and Non-Patent Document 1. However, the method is hardly suitable for industrial production.

DOCUMENT LIST

Patent Document

Patent Document 1: U.S. Pat. No. 4,367,344

Non-Patent Document

Non-Patent Document 1: Journal of Organic Chemistry (J. Org. Chem.) 1990, vol. 55, pages 4276-4281

SUMMARY OF THE INVENTION

The present invention provides a production method of 1-aminocyclopropanecarboxylic acid non-hydrate.

Treating 1-aminocyclopropanecarboxylic acid hydrochloride with a tertiary amine in the presence of a $C_3$-$C_4$ alcohol and water facilitates the crystallization of a free form of 1-aminocyclopropanecarboxylic acid 0.5 hydrate, while preventing the crystallization of the tertiary amine hydrochloride. In the present invention, first, the 0.5 hydrate superior in filtration property is obtained, and then is contacted with a $C_1$-$C_2$ alcohol to remove water from the 0.5 hydrate, whereby 1-aminocyclopropanecarboxylic acid non-hydrate is obtained.

Accordingly, the present invention provides the following.
[1] A method of producing 1-aminocyclopropanecarboxylic acid non-hydrate, which comprises
treating 1-aminocyclopropanecarboxylic acid hydrochloride with a tertiary amine in the presence of a $C_3$-$C_4$ alcohol and water, keeping the reaction mixture at 50° C. or below, collecting the precipitated crystal of 1-aminocyclopropanecarboxylic acid 0.5 hydrate by filtration, and contacting the obtained crystal with a $C_1$-02 alcohol.
[2] The method of the above-mentioned [1], wherein the $C_1$-$C_2$ alcohol is methanol.
[3] The method of the above-mentioned [1] or [2], which further comprises a step of subjecting a $C_1$-$C_4$ alkyl 1-acetylaminocyclopropanecarboxylate to hydrolysis using hydrochloric acid to obtain 1-aminocyclopropanecarboxylic acid hydrochloride.

According to the present invention, since a free form of 1-aminocyclopropanecarboxylic acid 0.5 hydrate, which is obtained from 1-aminocyclopropanecarboxylic acid hydrochloride, can be easily crystallized, it can be obtained in good yield in simple process. In addition, the 0.5 hydrate can be easily converted into the non-hydrate by contacting with a $C_1$-$C_2$ alcohol. The production method of the present invention can provide a free form of 1-aminocyclopropanecarboxylic acid non-hydrate with a high purity in simple process, and therefore, it is suitable for industrial production.

DESCRIPTION OF EMBODIMENTS

Figure 1:
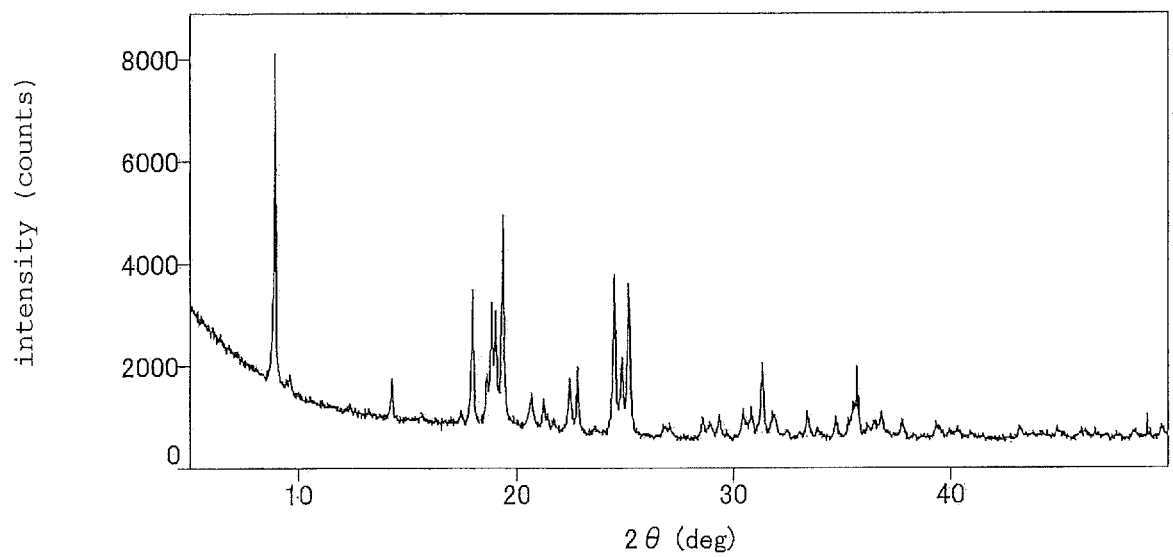
FIG. 1 shows X-RAY diffraction data of 1-aminocyclopropanecarboxylic acid 0.5 hydrate before contact with methanol.

The present invention is explained in detail below. 1-Aminocyclopropanecarboxylic acid hydrochloride can be obtained by subjecting 1-aminocyclopropanecarbonitrile to hydrolysis using hydrochloric acid, according to the description of Non-Patent Document 1. In addition, the compound can also obtained by subjecting ethyl 1-acetylaminocyclopropanecarboxylate to hydrolysis using hydrochloric acid, according to the description of Patent Document 1.

In the present invention, the treatment step with a tertiary amine is carried out advantageously on the 1-aminocyclopropanecarboxylic acid hydrochloride obtained by subjecting a $C_1$-$C_4$ alkyl 1-acetylaminocyclopropanecarboxylate to hydrolysis using hydrochloric acid.

The $C_1$-$C_4$ alkyl 1-acetylaminocyclopropanecarboxylate can be produced according to the description in Patent Document 1. The hydrolysis reaction is carried out according to a method known per se, for example by adding hydrochloric acid to a mixture of the $C_1$-$C_4$ alkyl 1-acetylaminocyclopropanecarboxylate and water, and then heating the mixture. The concentration of the hydrochloric acid is generally 1 to 25%, the reaction temperature is generally 70 to 110° C., and the reaction time is generally 0.5 to 24 hr. The amount of the hydrochloric acid to be used is generally 1.0 to 3.0 mol, preferably 1.5 to 2.0 mol, as a HCl amount, per 1 mol of the $C_1$-$C_4$ alkyl 1-acetylaminocyclopropanecarboxylate. The hydrolysis reaction may be carried out while evaporating acetic acid and methanol generated during the reaction, and methyl acetate generated by condensation of the acetic acid and methanol.

Thus obtained hydrochloric acid solution containing 1-aminocyclopropanecarboxylic acid hydrochloride may be directly used in the next treatment step with a tertiary amine, without isolation.

Examples of the $C_1$-$C_4$ alkyl ester include methyl ester, ethyl ester, 1-propyl ester, 2-propyl ester, 1-butyl ester, tert-butyl ester and the like, preferred are $C_1$-$C_2$ alkyl esters, and particularly preferred is a $C_1$ alkyl ester, i.e., methyl ester.

The step of treating 1-aminocyclopropanecarboxylic acid hydrochloride with a tertiary amine is explained below.

The term "$C_3$-$C_4$ alcohol" herein means an alcohol having 3 to 4 carbon atoms, and examples thereof include 1-propanol, 2-propanol, 1-butanol, 2-methylpropan-1-ol, 2-butanol and 2-methyl-2-propanol. Among them, preferred is 2-propanol in terms of crystallization efficiency of 1-aminocyclopropanecarboxylic acid 0.5 hydrate, miscibility with water, and solubility of the tertiary amine hydrochloride.

The amount of the $C_3$-$C_4$ alcohol to be used is generally 1 to 10 parts by weight, preferably 1 to 3 parts by weight from industrial aspect, per 1 part by weight of the 1-aminocyclopropanecarboxylic acid hydrochloride.

The amount of the water to be used is generally 1 to 10 parts by weight, preferably 1 to 3 parts by weight from industrial aspect, per 1 part by weight of the 1-aminocyclopropanecarboxylic acid hydrochloride. In addition, the amount is generally 0.5 to 2 parts by weight, per 1 part by weight of the $C_3$-$C_4$ alcohol, and the amount is determined so that the generated tertiary amine hydrochloride can be dissolved, depending on the kind of the alcohol, and the mixing ratio with the alcohol.

Examples of the tertiary amine include trimethylamine, triethylamine, N,N-diisopropylethylamine and the like. Among them, preferred is triethylamine in terms of easy handling, and high solubility of the generated tertiary amine hydrochloride in the mixture of a $C_3$-$C_4$ alcohol and water.

The amount of the tertiary amine to be used is an amount sufficient to adjust the pH of the reaction system to 5.0 to 7.0, preferably 5.5 to 6.5.

The treatment with a tertiary amine is generally carried out by mixing 1-aminocyclopropanecarboxylic acid hydrochloride, a $C_3$-$C_4$ alcohol, water and a tertiary amine. Specifically,
(1) a method of adding a tertiary amine to a mixture of 1-aminocyclopropanecarboxylic acid hydrochloride and a $C_3$-$C_4$ alcohol and water,
(2) a method of adding 1-aminocyclopropanecarboxylic acid hydrochloride (plus water if necessary) to a mixture of a $C_3$-$C_4$ alcohol and a tertiary amine (plus water if necessary), and
(3) a method of adding a $C_3$-$C_4$ alcohol to a mixture of 1-aminocyclopropanecarboxylic acid hydrochloride, a tertiary amine and water,
are exemplified. Among them, preferred are the methods of (1) and (2) in terms of purity of the obtained crystals. The addition may be dropwise addition. The addition is generally carried out at 10 to 100° C., preferably at 20 to 30° C.

After the treatment with a tertiary amine, by keeping the reaction mixture at 50° C. or below, generally at 40° C. or below, preferably at 10 to 40° C., more preferably at 20 to 30° C., preferably under stirring, 1-aminocyclopropanecarboxylic acid 0.5 hydrate is crystallized. The stirring is generally carried, out for 1 to 24 hr, preferably 2 to 15 hr.

The 0.5 hydrate is a stable and block-like crystal superior in filtration property relative to the non-hydrate being a micaceous crystal. Hence, with the 0.5 hydrate, the filtration step and washing step can be advantageously carried out in a short time, leaving much less amount of the tertiary amine.

The crystallization of the 0.5 hydrate can be facilitated by using seed crystals of the 0.5 hydrate.

The precipitated crystals are collected by filtration to obtain 1-aminocyclopropanecarboxylic acid 0.5 hydrate.

Thus obtained 1-aminocyclopropanecarboxylic acid 0.5 hydrate is converted into 1-aminocyclopropanecarboxylic acid non-hydrate by contacting with a $C_1$-$C_2$ alcohol.

The term "$C_1$-$C_2$ alcohol" herein means methanol or ethanol. Of these, preferred is methanol in terms of efficient removal of water from the crystal structure of the 0.5 hydrate.

The amount of the $C_1$-$C_2$ alcohol to be used is generally 0.5 to 5 parts by weight, preferably 0.5 to 2 parts by weight from industrial aspect, per 1 part by weight of 1-aminocyclopropanecarboxylic acid 0.5 hydrate, in terms of water removal efficiency and economic efficiency.

The contact of 1-aminocyclopropanecarboxylic acid 0.5 hydrate with a $C_1$-$C_2$ alcohol can be carried out by mixing 1-aminocyclopropanecarboxylic acid 0.5 hydrate and a $C_1$-$C_2$ alcohol, and then stirring the obtained mixture. Alternatively, the contact can also be carried out by washing or moistening 1-aminocyclopropanecarboxylic acid 0.5 hydrate with a $C_1$-$C_2$ alcohol. Washing or moistening 1-aminocyclopropanecarboxylic acid 0.5 hydrate with a $C_1$-$C_2$ alcohol is preferable method for the contact in terms of water removal efficiency and easy operation.

The contact of 1-aminocyclopropanecarboxylic acid 0.5 hydrate with a $C_1$-$C_2$ alcohol is carried out generally at 0 to 40° C., preferably at 10 to 30° C. from industrial aspect. The contact time is generally 10 min to 10 hr, preferably 10 min to 2 hr from industrial aspect.

After the contact of 1-aminocyclopropanecarboxylic acid 0.5 hydrate with a $C_1$-$C_2$ alcohol, the converted 1-aminocyclopropanecarboxylic acid non-hydrate may be dried if necessary. The drying is carried out generally at 80° C. or below, preferably at 60° C. or below, particularly preferably at 20 to 60° C., from industrial aspect. The drying may be carried out under stream of nitrogen gas and the like, and/or under reduced pressure of 20 kPa to 1 kPa. The drying time is generally 10 min to 20 hr, preferably 10 min to 10 hr from industrial aspect. Filtration may be carried out before the drying, but it can be omitted.

A preferable method for industrial production is to carry out, after the completion of the reaction producing 1-aminocyclopropanecarboxylic acid 0.5 hydrate, filtering the precipitated crystal of 1-aminocyclopropanecarboxylic acid 0.5 hydrate, followed by washing with a $C_1$-$C_2$ alcohol and then drying. Such a method offers a tremendous advantage in industrial production, because it allows to commence the method of the present invention continuously from the reaction producing 1-aminocyclopropanecarboxylic acid 0.5 hydrate, and also allows to eliminate the step of filtering 1-aminocyclopropanecarboxylic acid non-hydrate.

EXAMPLES

The present invention is concretely explained by referring to the following Examples, Reference Examples and Comparative Examples. In Examples, Reference Examples and Comparative Examples, the measurement conditions for Karl Fischer method and X-RAY diffraction (XRD) are as follows.

Water Content Measurement by Karl Fischer Method

The water content was measured by Karl Fischer method using coulometric Karl Fischer moisture analyzer (CA-200, Mitsubishi Chemical Analytech).

Measurement Conditions for X-RAY Diffraction (XRD)

X-RAY diffraction apparatus: SmartLab (Rigaku)

X-RAY output: CuKα, 45 kV, 200 mA sampling width: 0.02° scanning field: 5°-50°

Example 1

To 1-aminocyclopropanecarboxylic acid hydrochloride (purity 98.7%, 2 g) were added water (2.7 g) and 2-methylpropan-1-ol (4.6 g). Triethylamine (1.5 g) was added thereto to adjust the pH to 6.0, the obtained slurry was cooled to 20° C., and the precipitated crystals were collected by filtration. The obtained crystals were washed with 2-methylpropan-1-ol (10.6 g) to give 1-aminocyclopropanecarboxylic acid 0.5 hydrate.

Example 2

To a mixture of 1-aminocyclopropanecarboxylic acid hydrochloride (purity 84.7%, 2 g) and 10% hydrochloric acid (4.0 g) was added 2-propanol (5.5 g). To the obtained solution was added triethylamine (2.7 g) to adjust the pH to 5.6, the obtained slurry was cooled to 15° C., and the precipitated crystals were collected by filtration. The obtained wet crystals were washed with 2-propanol (1.7 g) to give 1-aminocyclopropanecarboxylic acid 0.5 hydrate.

Example 3

To a mixture of 1-aminocyclopropanecarboxylic acid hydrochloride (purity: 84.7%, 10 g) and 10% hydrochloric acid (4.0 g) was added 1-butanol (16.8 g). To the obtained solution was added triethylamine (13.2 g) to adjust the pH to 5.6, the obtained slurry was cooled to 16° C., and the precipitated crystals were collected by filtration. The obtained wet crystals were washed with 1-butanol (8.3 g), and dried under reduced pressure at 50° C. for 3 hr to give 1-aminocyclopropanecarboxylic acid 0.5 hydrate (5.83 g, content: 92.0% (yield 86.2%), water content: 8.0%).

Example 4

To methyl 1-acetylaminocyclopropanecarboxylate (purity 65%, 39.9 g) was added water (12.6 g), and the mixture was heated to 100° C. 35% Hydrochloric acid (28.3 g) was added dropwise thereto over 5 hr, and the mixture was kept at the same temperature for 10 hr to give a hydrochloric acid solution containing 1-aminocyclopropanecarboxylic acid hydrochloride (22.4 g, yield 98.4%).

To the obtained hydrochloric acid solution containing the crude 1-aminocyclopropanecarboxylic acid hydrochloride was added water (19.1 g), and the mixture was added dropwise to a mixture of 2-propanol (51.9 g), triethylamine (28.4 g), water (3.3 g) and 1-aminocyclopropanecarboxylic acid 0.5 hydrate (50 mg) over 5 hr at 25° C. After the completion of the addition, triethylamine was added thereto to adjust the pH to 6.0, and the mixture was stirred at 25° C. for 12 hr. A part of the precipitated crystals was separately collected by filtration. The crystal was confirmed to be 0.5 hydrate based on the water content measurement of the crystal.

Examples 5 and 6 and Comparative Examples 1 to 6

To 1-aminocyclopropanecarboxylic acid 0.5 hydrate (1 g), a solvent (0.5 g) was added as shown in Table 1, and the mixture was stirred well, followed by drying under reduced pressure of 1 kPa, at 22° C. for 1 hr. Then, the water content in the samples was measured by KF method. The results are shown in Table 1.

The term "conversion rate" herein means a rate at which 1-aminocyclopropanecarboxylic acid 0.5 hydrate is converted into 1-aminocyclopropanecarboxylic acid non-hydrate. The conversion rate (0%-100%) is calculated according to the following formula, using 8.2% which is the water content of 1-0.10 aminocyclopropanecarboxylic acid 0.5 hydrate as a reference:

Conversion rate (%)={8.2%-water content (%)/8.2%}×100

TABLE 1

| | solvent | water content (KF method) | conversion rate |
|---|---|---|---|
| | none | 8.2% | — |
| Example 5 | methanol | 4.6% | 43% |
| Example 6 | ethanol | 5.1% | 38% |
| Comparative Example 1 | toluene | 8.1% | 1% |
| Comparative Example 2 | hexane | 8.1% | 1% |
| Comparative Example 3 | heptane | 8.5% | 0% |
| Comparative Example 4 | acetone | 8.2% | 0% |
| Comparative Example 5 | acetonitrile | 8.0% | 2% |
| Comparative Example 6 | ethyl acetate | 8.2% | 0% |

Example 7

Figure 2:
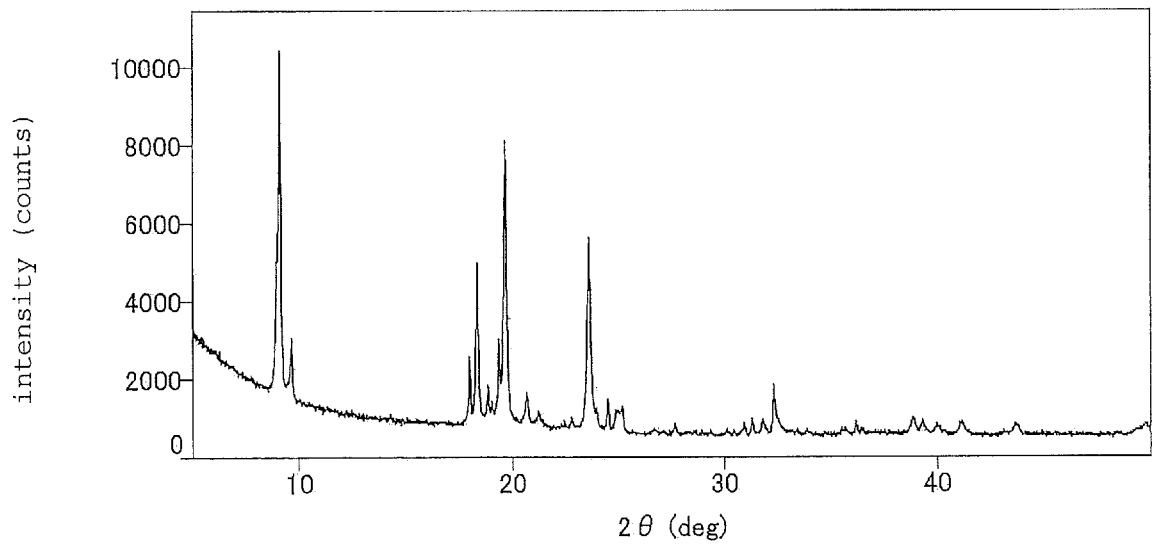
FIG. 2 shows X-RAY diffraction data of 1-aminocyclopropanecarboxylic acid 0.5 hydrate immediately after contact with methanol.
Figure 3:
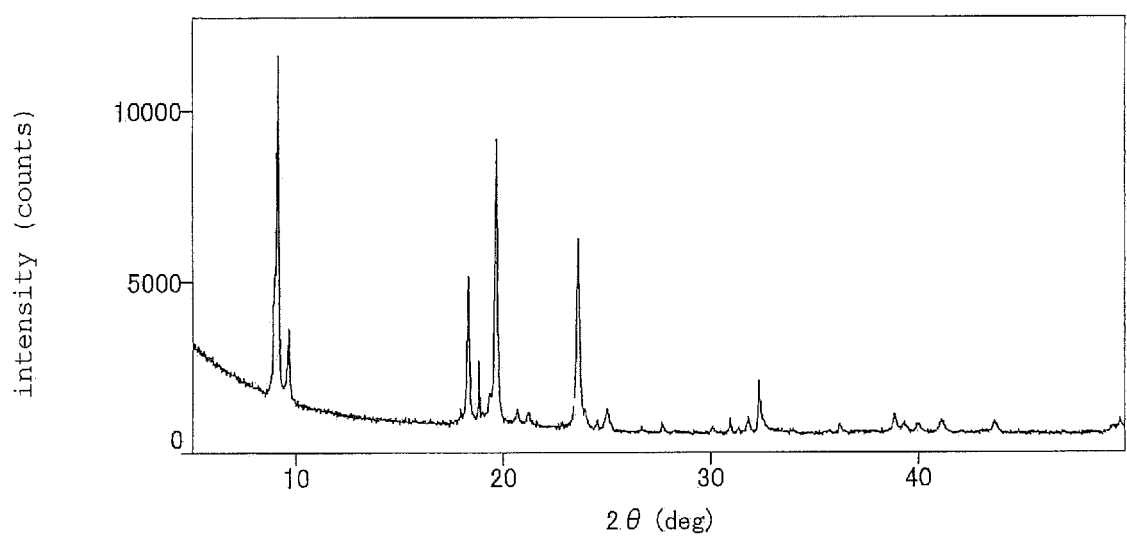
FIG. 3 shows X-RAY diffraction data of 1-aminocyclopropanecarboxylic acid 0.5 hydrate after eight minutes of contact with methanol.

The structure of a crystal of 1-aminocyclopropanecarboxylic acid 0.5 hydrate was confirmed by X-RAY diffraction (XRD). After spraying methanol on the 0.5 hydrate, a flow of nitrogen gas was used to observe how the crystal structure changes as time passes. FIGS. 1 to 3 show XRD data. Immediately after the gas flow was started, transition of crystal structure to the non-hydrate was initiated, and the crystal was confirmed to have converted almost entirely to non-hydrate after eight minutes of the nitrogen gas flow.

Reference Example

To 1-aminocyclopropanecarboxylic acid 0.5 hydrate (0.5 g) was added methanol (4.5 g, water content 58 ppm), and the mixture was stirred at 30° C. for 30 min. The water content of the supernatant methanol was measured by KF method, and the reading was 0.88% (i.e., 96.7% of the water content in the 0.5 hydrate).

INDUSTRIAL APPLICABILITY

According to the present invention, 1-aminocyclopropanecarboxylic acid 0.5 hydrate can be obtained in simple process from 1-aminocyclopropanecarboxylic acid hydrochloride. Moreover, 1-aminocyclopropanecarboxylic acid non-hydrate being a plant growth regulator can be easily obtained by contacting with a $C_1$-$C_2$ alcohol.

The invention claimed is:

1. A method of producing 1-aminocyclopropanecarboxylic acid non-hydrate, which comprises
    treating 1-aminocyclopropanecarboxylic acid hydrochloride with a tertiary amine in the presence of a $C_3$-$C_4$ alcohol and water,
    keeping the reaction mixture at 50° C. or below,
    collecting the precipitated crystal of 1-aminocyclopropanecarboxylic acid 0.5 hydrate by filtration, and
    contacting the obtained crystal with a $C_1$-$C_2$ alcohol.

2. The method according to claim 1, wherein the $C_1$-$C_2$ alcohol is methanol.

3. The method according to claim 1, which further comprises a step of subjecting a $C_1$-$C_4$ alkyl 1-acetylaminocyclopropanecarboxylate to hydrolysis using hydrochloric acid to obtain 1-aminocyclopropanecarboxylic acid hydrochloride.

\* \* \* \* \*